United States Patent [19]

Föry

[11] Patent Number: 4,560,771

[45] Date of Patent: Dec. 24, 1985

[54] PROCESS FOR THE PREPARATION OF 1,2-BENZOXATHIINES

[75] Inventor: Werner Föry, Basel, Switzerland

[73] Assignee: Ciba Geigy Corporation, Ardsley, N.Y.

[21] Appl. No.: 656,192

[22] Filed: Oct. 1, 1984

[51] Int. Cl.⁴ .......................................... C07D 327/06
[52] U.S. Cl. ...................................... 549/15; 549/466; 549/467; 549/468; 549/469; 544/212; 544/297
[58] Field of Search ................. 549/15, 466, 467, 468, 549/469

[56] References Cited

FOREIGN PATENT DOCUMENTS

| 0099339 | 1/1984 | European Pat. Off. | 549/15 |
| 0107979 | 5/1984 | European Pat. Off. | 549/15 |
| 0128116 | 7/1984 | European Pat. Off. | 549/15 |

OTHER PUBLICATIONS

Clancy et al., C.A., vol. 79, 1973, 79:105159t.

*Primary Examiner*—Henry R. Jiles
*Assistant Examiner*—J. G. Mullins
*Attorney, Agent, or Firm*—Karl F. Jorda

[57] ABSTRACT 1,2-Benzoxathiine derivatives of the formula I

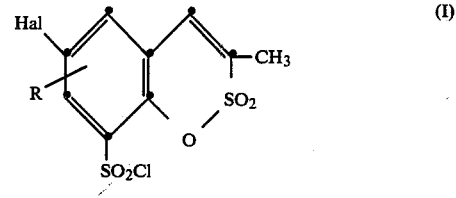

wherein
Hal is chlorine, bromine or iodine,
R is hydrogen, halogen, nitro, $C_1$-$C_4$alkyl, $C_1$-$C_4$haloalkyl, cyano or a —X—$R^1$, —CO—X—$R^2$, —CO—$NR^3R^4$, —SO—$R^5$ or —$SO_2$—$R^6$ group, where
$R^1$ is $C_3$-$C_5$alkynyl, or is $C_1$-$C_4$alkyl, unsubstituted or substituted by halogen or $C_1$-$C_4$alkoxy, or is $C_3$-$C_5$alkenyl, unsubstituted or substituted by halogen or $C_1$-$C_4$alkyoxy,
$R^2$ and $R^5$ are each independently of the other $C_1$-$C_4$alkyl, $C_1$-$C_4$haloalkyl, $C_2$-$C_4$alkoxyalkyl, $C_3$-$C_5$alkenyl, $C_3$-$C_5$alkynyl, phenyl or benzyl,
$R^3$ and $R^4$ are each independently of the other hydrogen, $C_1$-$C_4$alkyl, $C_1$-$C_4$haloalkyl, $C_2$-$C_4$alkoxyalkyl, $C_3$-$C_5$alkenyl, $C_3$-$C_5$alkynyl, phenyl or benzyl, $R^6$ is $C_1$-$C_4$alkyl, $C_1$-$C_4$alkoxy, $C_1$-$C_4$haloalkoxy or —$NR^7R^8$,
$R^7$ and $R^8$ are each independently of the other hydrogen, $C_1$-$C_4$alkyl, $C_1$-$C_4$haloalkyl, $C_2$-$C_4$alkoxyalkyl, $C_3$-$C_5$alkenyl, $C_3$-$C_5$alkynyl, phenyl or benzyl, and
X is oxygen or sulfur, are obtained by treating a dihydrobenzofuran derivative of formula II

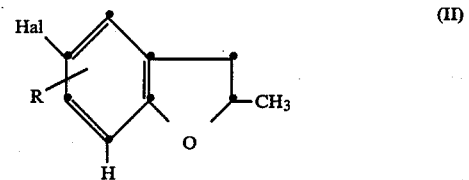

with chlorosulfonic acid of the formula $ClSO_3H$.

8 Claims, No Drawings

PROCESS FOR THE PREPARATION OF 1,2-BENZOXATHIINES

The present invention relates to a process for the preparation of 8-sulfonyl-1,2-benzoxathiine derivatives.

The 8-sulfonyl-1,2-benzoxathiine derivatives obtainable by the process of this invention are valuable intermediates for the preparation of herbicides and plant growth regulators of the class of the sulfonylureas. Such compounds and their biological properties are known for example from published European patent application EP-A-No.99 339 and No. 84810215.8.

The preparation of compounds having the 1,2-benzoxathiine structure has been described in various publications: Int. J. Sulfur Chem., A, Volume 2, No. 4, 249–255 (1972) or EP-A-No.107 979. The procedures employed are poorly suited to large-scale production, as they proceed via a relatively large number of process steps.

Accordingly, there is a need for a simple synthesis comprising a few reaction steps and permitting the production of the desired intermediates in good yield.

Surprisingly, it has now been found that it is possible to prepare 1,2-benzoxathiine derivatives of the formula I

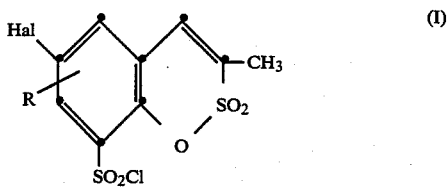

wherein
Hal is chlorine, bromine or iodine,
R is hydrogen, halogen, nitro, $C_1$–$C_4$alkyl, $C_1$–$C_4$haloalkyl, cyano or a —X—$R^1$, —CO—X—$R^2$, —CO—$NR^3R^4$, —SO—$R^5$ or —$SO_2$—$R^6$ group, where
$R^1$ is $C_3$–$C_5$alkynyl, or is $C_1$–$C_4$alkyl, unsubstituted or substituted by halogen or $C_1$–$C_4$alkoxy, or is $C_3$–$C_5$alkenyl, unsubstituted or substituted by halogen or $C_1$–$C_4$alkoxy,
$R^2$ and $R^5$ are each independently of the other $C_1$–$C_4$alkyl, $C_1$–$C_4$haloalkyl, $C_2$–$C_4$alkoxyalkyl, $C_3$–$C_5$alkenyl, $C_3$–$C_5$alkynyl, phenyl or benzyl,
$R^3$ and $R^4$ are each independently of the other hydrogen, $C_1$–$C_4$alkyl, $C_1$–$C_4$haloalkyl, $C_2$–$C_4$alkoxyalkyl, $C_3$–$C_5$alkenyl, $C_3$–$C_5$alkynyl, phenyl or benzyl,
$R^6$ is $C_1$–$C_4$alkyl, $C_1$–$C_4$alkoxy, $C_1$–$C_4$haloalkoxy or —$NR^7R^8$,
$R^7$ and $R^8$ are each independently of the other hydrogen, $C_1$–$C_4$alkyl, $C_1$–$C_4$haloalkyl, $C_2$–$C_4$alkoxyalkyl, $C_3$–$C_5$alkenyl, $C_3$–$C_5$alkynyl, phenyl or benzyl, and
X is oxygen or sulfur,
by treating a dihydrobenzofuran derivative of the formula II

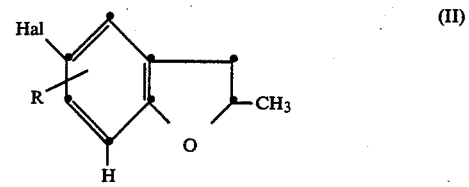

with chlorosulfonic acid of the formula $ClSO_3H$. Within the scope of the present invention, halogen both by itself or as moiety of a radical such as haloalkyl denotes fluorine, chlorine, bromine or iodine. Fluorine and chlorine are preferred. Alkyl is straight chain or branched alkyl, e.g. methyl, ethyl, n-propyl, isopropyl or the four butyl isomers, with methyl, ethyl and isopropyl being preferred. Alkoxy will be generally understood to mean methoxy, ethoxy, n-propoxy, isopropoxy or the four butoxy isomers. Alkenyl is usually allyl, 2-butenyl, 3-butenyl or methallyl; and alkynyl is propargyl, 2-butynyl or 3-butynyl. Within the scope of the above definitions, alkoxyalkyl comprises: methoxymethyl, methoxyethyl, methoxypropyl, ethoxymethyl, ethoxyethyl and propoxymethyl. Preferred examples of haloalkyl are fluoromethyl, difluoromethyl, trifluoromethyl, 2,2,2-trifluoromethyl, 1,1,2,2-tetrafluoroethyl, perfluoroethyl, 2-chloroethyl, 2,2,2-trichloroethyl, 3,3,3-trifluoropropyl or 1,1,2,3,3,3-hexafluoropropyl. Haloalkyl will also be understood as being moiety of a haloalkoxy or haloalkylthio substituent. In the process of this invention there will preferably be obtained those compounds in which Hal is chlorine or bromine and R is hydrogen or $C_1$–$C_4$alkyl.

The reaction products of the formula I can be converted into herbicidal and plant growth regulating sulfonylurea derivatives by methods analogous to those known in the literature, for example by converting the sulfonyl chloride group into the sulfonamide group with ammonia and reacting resultant derivatives of the formula III

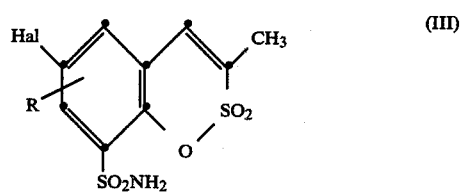

in known manner, either direct or, for example, in the form of the corresponding carbamate, to give a sulfonylurea. The intermediates of formula III can also be converted by methods known per se into further intermediates (of formulae IV and V) for preparing highly effective herbicides of the class of the sulfonylureas.

Thus, for example, a compound of the formula IV

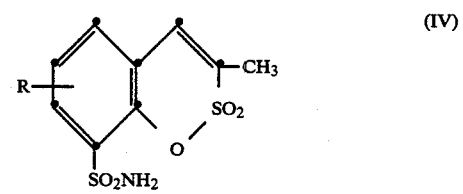

wherein R is as defined for formula I, is obtained by dehalogenating a compound of formula III, in known manner, with hydrogen.

Further, a compound of formula V

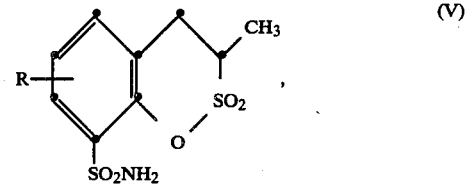

wherein R is as defined for formula I, is obtained by hydrogenating a compound of formula IV with hydrogen in the presence of a noble metal catalyst.

The intermediates of formula IV and V can be converted into effective herbicides of the class of the sulfonylureas by methods analogous to those described for obtaining compounds of formula III. Commercially available chlorosulfonic acid is employed for carrying out the process of this invention for the preparation of compounds of formula I. At least 3 moles of chlorosulfonic acid are used per mole of compound of formula II. It is convenient to use a substantial excess, for example at least 5 moles, of chlorosulfonic acid per mole of compound II. In individual cases, the chlorosulfonic acid can be used simultaneously as reactant and as solvent. In general, however, the reaction is carried out in an inert solvent. Suitable solvents are carbon disulfide, ethyl acetate, and chlorinated hydrocarbons such as methylene chloride, chloroform, carbon tetrachloride, 1,2-dichloroethane, 1,2-dichloroethylene, tetrachloroethylene, chlorobenzene or dichlorobenzene. The preferred solvents are methylene chloride, 1,2-dichloroethane and chloroform. The reaction temperatures are normally in the range from −10° to +80° C., preferably from −10° to +60° C.

In a preferred embodiment of the invention, the compounds of formula I, wherein Hal is chlorine or bromine and R is hydrogen or $C_1$–$C_4$-alkyl, are prepared by reacting an appropriate compound of formula II with at least 3 moles of chlorosulfonic acid per mole of compound of formula II, in an inert solvent and in the temperature range from −10° to +80° C.

The most preferred embodiment of the process of the invention is that in which the reaction is carried out in the temperature range from −10° to +60° C. in methylene chloride, 1,2-dichloroethane or chloroform, with at least 5 moles of chlorosulfonic acid per mole of compound of formula II.

The optional conversion reactions to give compounds of the formulae III, IV or V are conducted under the reaction conditions conventionally employed for these per se known reactions. Accordingly, the compounds of formula III are normally obtained by treating compound I with an aqueous solution of ammonia under normal pressure at room temperature. The dehalogenation of the compound III to give the compound IV by catalytic hydrogenation is generally carried out at room temperature under normal pressure in an inert solvent and in the presence of an acid acceptor, preferably a tertiary amine, for example triethylamine. The catalytic hydrogenation of the non-aromatic double bond of the compound IV to give the compound V is carried out under more severe conditions: both the pressure of the hydrogen atmosphere and the temperature are increased (to 1 to 10 bar and 30° to 60° C. respectively). Suitable hydrogenation or dehalogenation catalysts are: platinum or palladium in the form of platinum oxide, platinum black, platinum or barium sulfate, palladium black or palladium on carbon. The most widely used catalyst is palladium on carbon in commercial form as 5% palladium/carbon.

The compounds obtainable by the process of this invention are for example those of formula I listed in Table 1

TABLE 1

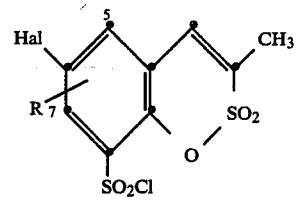

| Compound No. | Hal | R |
|---|---|---|
| 1.1 | Cl | H |
| 1.2 | Br | H |
| 1.3 | Cl | 7-$CH_3$ |
| 1.4 | Cl | 5-$CH_3$ |
| 1.5 | Cl | 5-$C_2H_5$ |
| 1.6 | Cl | 7-$C_2H_5$ |
| 1.7 | Br | 7-$CH_3$ |
| 1.8 | Br | 7-$C_2H_5$ |
| 1.9 | Br | 7-$C_3H_7$—i |
| 1.10 | Br | 5-$CH_3$ |
| 1.11 | Br | 5-$C_2H_5$ |
| 1.12 | Br | 5-$NO_2$ |
| 1.13 | Br | 5-Br |
| 1.14 | Br | 5-Cl |
| 1.15 | Br | 5-CN |

The intermediates listed in Tables 2 to 4 (in the sulfonamide stage) can be obtained from the above compounds by optional subsequent operations for preparing herbicidally effective sulfonylureas.

TABLE 2

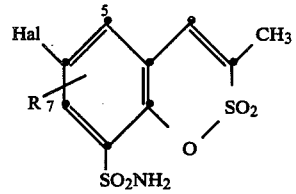

| Compound No. | Hal | R |
|---|---|---|
| 2.1 | Cl | H |
| 2.2 | Br | H |
| 2.3 | Cl | 7-$CH_3$ |
| 2.4 | Cl | 5-$CH_3$ |
| 2.5 | Cl | 5-$C_2H_5$ |
| 2.6 | Cl | 7-$C_2H_5$ |
| 2.7 | Br | 7-$CH_3$ |
| 2.8 | Br | 7-$C_2H_5$ |
| 2.9 | Br | 7-$C_3H_7$—i |
| 2.10 | Br | 5-$CH_3$ |
| 2.11 | Br | 5-$C_2H_5$ |
| 2.12 | Br | 5-$NO_2$ |
| 2.13 | Br | 5-Br |
| 2.14 | Br | 5-Cl |
| 2.15 | Br | 5-CN |

TABLE 3

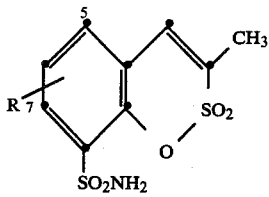

| Compound No. | R |
|---|---|
| 3.1 | H |
| 3.2 | 7-CH$_3$ |
| 3.3 | 7-C$_2$H$_5$ |
| 3.4 | 5-CH$_3$ |
| 3.5 | 5-C$_2$H$_5$ |
| 3.6 | 5-Cl |
| 3.7 | 5-CN |
| 3.8 | 7-C$_3$H$_7$—i |

TABLE 4

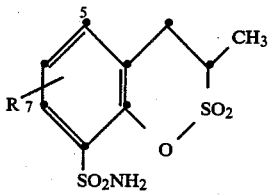

| Compound No. | R |
|---|---|
| 4.1 | H |
| 4.2 | 7-CH$_3$ |
| 4.3 | 7-C$_2$H$_5$ |
| 4.4 | 5-CH$_3$ |
| 4.5 | 5-C$_2$H$_5$ |
| 4.6 | 5-Cl |
| 4.7 | 5-CN |
| 4.8 | 7-C$_3$H$_7$—i |

The following Examples P1 to P7 will serve to illustrate the invention in more detail.

PREPARATORY EXAMPLES

Example P1

6-Bromo-2,2-dioxo-3-methyl-1,2-benzoxathiin-8-ylsulfonamide (a) 5-Bromo-2,3-dihydro-2-methylbenzo[b]furan A solution of 215 ml of bromine in 450 ml of methylene chloride is added dropwise over 2½ hours to an ice-cooled mixture of 562.3 g of 2,3-dihydro-2-methylbenzo[b]furan, 1600 ml of methylene chloride, 1600 ml of water and 352.5 g of sodium bicarbonate. After the mixture has been stirred for another 1½ hours at the same temperature, the aqueous phase is separated and extracted with two 300 ml portions of methylene chloride. The combined organic phases are washed with 2×250 ml of water, dried over sodium sulfate and concentrated. After removal of all constituents having a boiling point below 99° C. under a pressure of 8 mbar, there are obtained 750.7 g of 5-bromo-2,3-dihydro-2-methylbenzo[b]furan as residue.

(b) 6-Bromo-2,2-dioxo-3-methyl-1,3-benzoxathiin-8-ylsulfonylchloride 400 ml of chlorosulfonic acid are added dropwise over 20 minutes to a solution of 160 g of 5-bromo-2,3-dihydro-2-methylbenzo[b]furan in 460 ml of absolute chloroform, which solution has been cooled to −7° C. The mixture is stirred at a temperature of 15° C. for 15 minutes and then stirred dropwise over 35 minutes into a mixture of 1.5 kg of ice, 1000 ml of water and 500 ml of chloroform. After this mixture has been stirred for 15 minutes at 0° C., the organic phase is separated and the aqueous phase is extracted with 3×250 ml of chloroform. The combined organic extracts are washed with 150 ml of water, dried over sodium sulfate and concentrated, affording 180 g of 6-bromo-2,2-dioxo-3-methyl-1,2-benzoxathiin-8-ylsulfonyl chloride as oily residue which can be further processed direct.

(c) A solution of 180 g of 6-bromo-2,2-dioxo-3-methyl-1,2-benzoxathiin-8-ylsulfonyl chloride in 500 ml of tetrahydrofuran is added dropwise over 30 minutes to 307 ml of a 30% aqueous solution of ammonia. The mixture is stirred for 30 minutes at 20° C. and concentrated under reduced pressure at 45° C. The residue is triturated with 200 ml of ether. The precipitate is isolated, washed with water and dried at 45° C., affording 63.2 g of 6-bromo-2,2-dioxo-3-methyl-1,2-benzoxathiin-8-ylsulfonamide of m.p. 243°–245° C. (recrystallisation from ethanol).

Example P2

6-Bromo-2,2-dioxo-3-methyl-1,2-benzoxathiin-8-ylsulfonamide (a) 6-Bromo-2,2-dioxo-3-methyl-1,2-benzoxathiin-8-ylsulfonyl chloride 133 ml of chlorosulfonic acid are added dropwise at a temperature from 40° to 50° C. over 30 minutes to a solution of 42.6 g of 5-bromo-2,3-dihydro-2-methylbenzo[b]furan in 120 ml of chloroform. The mixture is heated to reflux for 4 hours and, after being cooled to 0° C., added dropwise over 30 minutes to a mixture of 400 g of ice, 500 ml of water and 100 ml of chloroform. The organic phase is separated and the aqueous phase is extracted with 3×100 ml of chloroform. The combined organic phases are washed with water and concentrated, affording 72.2 g of 6-bromo-2,2-dioxo-3-methyl-1,2-benzoxathiin-8-ylsulfonyl chloride as oily residue.

(b) 72.2 g of 6-bromo-2,2-dioxo-3-methyl-1,2-benzoxathiin-8-ylsulfonyl chloride are dissolved in 200 ml of tetrahydrofuran and the solution is added dropwise to 122.6 ml of a 30% aqueous solution of ammonia. The mixture is stirred for 30 minutes at 20° C. and concentrated under reduced pressure at 45° C. The residue is triturated with ether. The precipitate so obtained is isolated, washed with water and dried at 45° C., affording 44.6 g of 6-bromo-2,2-dioxo-3-methyl-1,2-benzoxathiin-8-ylsulfonamide.

Example P3

2,2-Dioxo-3-methyl-1,2-benzoxathiin-8-ylsulfonamide 120 g of 6-bromo-2,2-dioxo-3-methyl-1,2-benzoxathiin-8-ylsulfonamide are dissolved in 2.4 liters of tetrahydrofuran and the solution is hydrogenated with hydrogen for 40 minutes, in the presence of 41.3 g of triethylamine and 12.0 g of 5% on carbon catalyst, under normal pressure and in the temperature range from 20° to 25° C. The mixture is filtered, the filtrate is concentrated, and the residue is taken up in 1300 ml of hot 90% aqueous ethanol. The insoluble constituents are separated and the solution is cooled to 0° C. The precipitate is separated and dried, affording 70 g of 2,2-dioxo-3-methyl-1,2-benzoxathiin-8-ylsulfonamide of m.p. 204°–205° C.

Example P4

3,4-Dihydro-2,2-dioxo-3-methyl-1,2-benzoxathiin-8-yl-sulfonamide 10.0 g of 2,2-dioxo-4-methyl-1,2-benzoxathiin-8-ylsulfonamide are dissolved in 200 ml of tetrahydrofuran and the solution is hydrogenated with hydrogen for 2½ hours, in the presence of 2.0 g of 5% palladium on carbon catalyst, under a pressure of 4 bar and at a temperature of 40° C. After removal of the catalyst the solution is concentrated and the residue is crystallised from 120 ml of 70% aqueous ethanol, affording 9.0 g of 3,4-dihydro-2,2-dioxo-3-methyl-1,2-benzoxathiin-8-ylsulfonamide of m.p. 185°–186° C.

Example P5

N-(3,4-Dihydro-2,2-dioxo-3-methyl-1,2-benzoxathiin-8-ylsulfonyl)-N'-(4-methoxy-6-methylpyrimidin-2-yl)urea A mixture of 3.33 g of 3,4-dihydro-2,2-dioxo-3-methyl-1,2-benzoxathiin-8-ylsulfonamide, 1.84 ml of 1,8-diazabicyclo[5.4.0]undec-7-ene, 3.2 g of N-(4-methoxy-6-methylpyrimidin-2-yl)phenylcarbamate and 35 ml of absolute dioxan is stirred for 45 minutes at a temperature in the range from 20° to 25° C. The mixture is concentrated and the oily residue is triturated with ether and 14 ml of 1N hydrochloric acid. The crystalline precipitate obtained is isolated, washed with water and dried, affording 4.96 g of N-(3,4-dihydro-2,2-dioxo-3-methyl-1,2-benzoxathiin-8-ylsulfonyl)-N'-(4-methoxy-6-methylpyrimidin-2-yl)urea of m.p. 215°–218° C.

Example P6

N-(6-Bromo-2,2-dioxo-3-methyl-1,2-benzoxathiin-8-ylsulfonyl)-N'-(4'-methoxy-6-methyl-1,3,5-triazin-2-yl)urea A reaction mixture of 3.54 g of 6-bromo-2,2-dioxo-3-methyl-1,2-benzoxathiin-8-ylsulfonamide, 1.61 ml of 1,8-diazabicyclo[5.4.0]undec-7-ene, 2.73 g of N-(4-methoxy-6-methyl-1,3,5-triazin-2-yl)phenylcarbamate and 35 ml of absolute dioxan is stirred for 1½ hours at room temperature. The solvent is evaporated and the oily residue is triturated with 10 ml of 1N hydrochloric acid and 5 ml of water. The precipitate is isolated by filtration, washed with ether and dried, affording 4.84 g of N-(6-bromo-2,2-dioxo-3-methyl-1,2-benzoxathiin-8ylsulfonyl)-N'-(4-methoxy-6-methyl-1,3,5-triazin-2-yl)urea of m.p. 196°–198° C.

Example P7

N-(2,2-Dioxo-3-methyl-1,2-benzoxathiin-8-ylsulfonyl)-N'-(4-methoxy-6-methyl-1,3,5-triazin-2-yl)urea A mixture of 3.3 g of 2,2-dioxo-3-methyl-1,2-benzoxathiin-8-yl sulfonamide, 1.90 ml of 1,8-diazabicyclo[5.4.-0]undec-7-ene, 3.28 g of N-(4-methoxy-6-methyl-1,3,5-triazin-2-yl)phenylcarbamate in a mixture of 25 ml of dioxan and 10 ml of acetonitrile is stirred at 20° C. to 25° C. for 1 hour. The solvents are evaporated and the residue is triturated with a mixture of 7 ml of 2N hydrochloric acid and 10 ml of water and then with 20 ml of ether. The precipitate is isolated by filtration and dried, affording 5.14 g of N-(2,2-dioxo-3-methyl-1,2-benzoxathiin-8-ylsulfonyl)-N'-(4-methoxy-6-methyl-1,3,5-triazin-2-yl)urea of m.p. 203°–205° C.

What is claimed is:

1. A process for the preparation of a 1,2-benzoxathiine derivative of the formula I

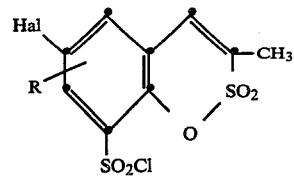

wherein

Hal is chlorine, bromine or iodine,

R is hydrogen, halogen, nitro, $C_1$-$C_4$alkyl, $C_1$-$C_4$-haloalkyl, cyano or a —X—$R^1$, —CO—X—$R^2$, —CO—$NR^3R^4$, —SO—$R^5$ or —$SO_2$—$R^6$ group, where $R^1$ is $C_3$-$C_5$alkynyl, or is $C_1$-$C_4$alkyl, unsubstituted or substituted by halogen or $C_1$-$C_4$alkoxy, or is $C_3$-$C_5$alkenyl, unsubstituted or substituted by halogen or $C_1$-$C_4$alkoxy, $R^2$ and $R^5$ are each independently of the other $C_1$-$C_4$alkyl, $C_1$-$C_4$haloalkyl, $C_2$-$C_4$alkoxyalkyl, $C_3$-$C_5$alkenyl, $C_3$-$C_5$alkynyl, phenyl or benzyl, $R^3$ and $R^4$ are each independently of the other hydrogen, $C_1$-$C_4$-alkyl, $C_1$-$C_4$haloalkyl, $C_2$-$C_4$alkoxyalkyl, $C_3$-$C_5$alkenyl, $C_3$-$C_5$alkynyl, phenyl or benzyl, $R^6$ is $C_1$-$C_4$alkyl, $C_1$-$C_4$alkoxy, $C_1$-$C_4$haloalkoxy or —$NR^7R^8$, $R^7$ and $R^8$ are each independently of the other hydrogen, $C_1$-$C_4$alkyl, $C_1$-$C_4$haloalkyl, $C_2$-$C_4$alkoxyalkyl, $C_3$-$C_5$alkenyl, $C_3$-$C_5$alkynyl, phenyl or benzyl, and X is oxygen or sulfur, which process comprises treating a dihydrobenzofuran derivative of formula II

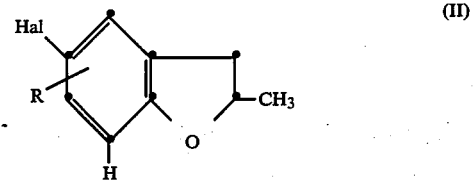

with chlorosulfonic acid of the formula $ClSO_3H$.

2. A process according to claim 1, wherein Hal is chlorine or bromine and R is hydrogen or $C_1$-$C_4$alkyl.

3. A process according to claim 1, wherein the reaction is carried out in the temperature range from −10° to +80° C., preferably from −10° C. to +60° C.

4. A process according to claim 1, wherein the reaction is carried out in an inert solvent.

5. A process according to claim 4, wherein the reaction is carried out in 1,2-dichloroethane, methylene chloride or chloroform.

6. A process according to claim 1, wherein at least 3 moles, preferably at least 5 moles, of chlorosulfonic acid are used per mole of compound of formula II.

7. A process according to claim 1, which comprises preparing a compound of the formula I, wherein Hal is chlorine or bromine and R is hydrogen or $C_1$-$C_4$alkyl, by reacting an appropriate compound of formula II with at least 3 moles of chlorosulfonic acid per mole of the compound of formula II, in an inert solvent solvent and in the temperature range from −10° to +80° C.

8. A process according to claim 7, wherein the reaction is carried out with at least 5 moles of chlorosulfonic acid per mole of the compound of formula II, in the temperature range from −10° to +60° C. in 1,2-dichloroethane, methylene chloride or chloroform.

* * * * *